United States Patent [19]

Walski

[11] 4,316,459
[45] Feb. 23, 1982

[54] ENDOTRACHEAL TUBE NOT REQUIRING ADHESIVE TAPE

[76] Inventor: Donald J. Walski, 5733 North Kenmore, Chicago, Ill. 60660

[21] Appl. No.: 65,128

[22] Filed: Aug. 9, 1979

[51] Int. Cl.³ ............................................ A61M 16/00
[52] U.S. Cl. .................................................. 128/207.17
[58] Field of Search .................... 128/207.14, 207.15, 128/207.17, DIG. 26, 348

[56] References Cited

U.S. PATENT DOCUMENTS

| | | | |
|---|---|---|---|
| 507,813 | 10/1893 | Hartstein | 128/207.14 |
| 3,602,227 | 7/1969 | Andrew | 128/207.17 |
| 3,927,676 | 12/1975 | Schultz | 128/207.17 |
| 4,167,946 | 9/1979 | Sandstrom | 128/207.17 |
| 4,223,671 | 9/1980 | Muto | 128/207.17 |

Primary Examiner—Hiram Bernstein
Attorney, Agent, or Firm—Eugene F. Friedman

[57] ABSTRACT

An endotracheal device composed of a tube and an adaptor press-fit together. The adaptor includes two flanges, each having a hole passing through it. A long ribbon of cloth passes through the holes in each of the flanges, wraps around the tube itself, and extends around the head of the patient. Tying the ends of the ribbon together secures the endotracheal device in its proper position without the use of adhesive tape. It also assists in retaining the adaptor onto the tube.

6 Claims, 5 Drawing Figures

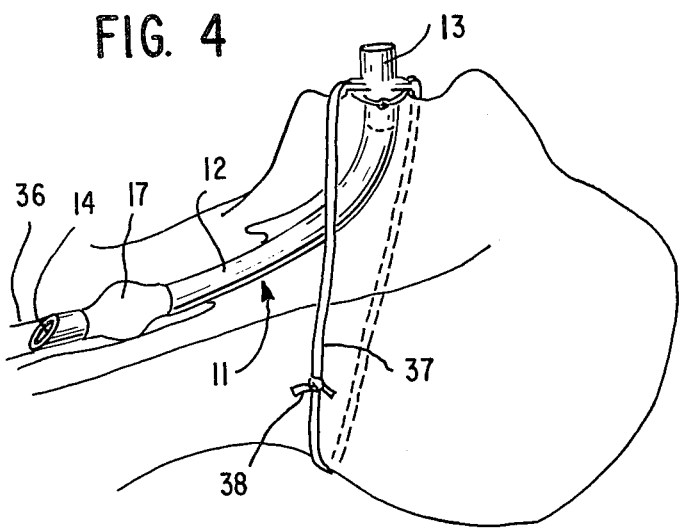
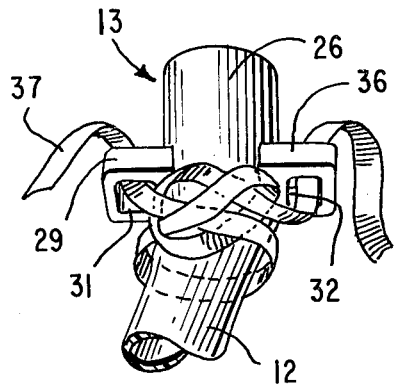
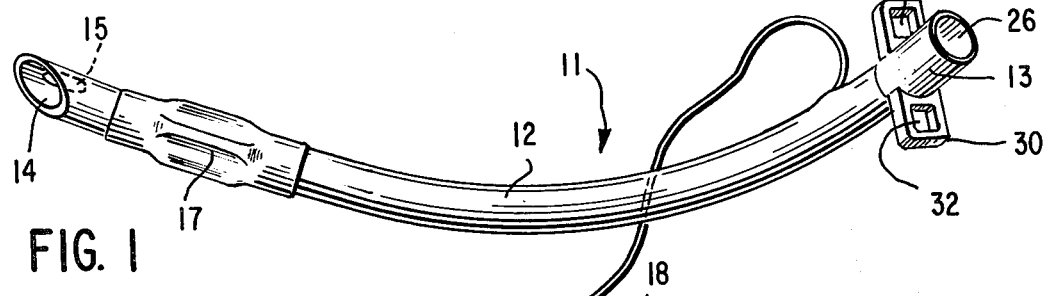
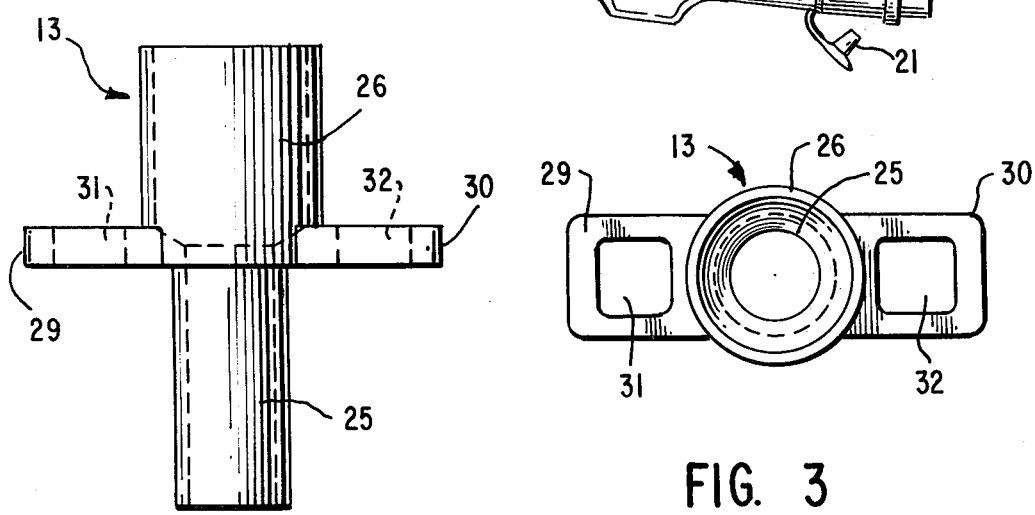

ENDOTRACHEAL TUBE NOT REQUIRING ADHESIVE TAPE

BACKGROUND

An endotracheal tube enters the treachea of a patient through the mouth or nose. It permits the external control of that person's breathing. The procedure provides important benefits when attaching a person, whose processes do not provide sufficient oxygen, to a respirator. It also finds use in administering a gaseous anesthetic to a patient undergoing a surgical procedure.

Typically, the endotracheal device includes a tube of semiflexible plastic shaped at one end to facilitate its insertion into the trachea. The other end couples to an adaptor with a press-fit coupling. The adaptor represents a piece of substantially rigid plastic which can connect to the mechanical respirating equipment.

To retain the endotracheal device in place, the tube usually includes an inflatable collar around the end inserted in the trachea. Once positioned in the trachea, the collar undergoes inflation to secure it against the tracheal wall. This helps to prevent its dislodgement from the desired location, and provides an airtight system.

Furthermore, the attendant generally places adhesive tape around the end of the device remaining extended from the patient's mouth. The tape wraps around the tube and then adheres to the patient's facial skin. The tape retains the tube in the proper position relative to the patient.

However, while intubated, the patient continues to salivate. These liquids, or "juices", flow up and around the tube and contact the adhesive tape. This fluid can then dislodge the tape from the tube, the adaptor, and the patient's face. Any benefit originally received from the tape becomes lost through this process. Moreover, the saliva can actually attack the press fit between the tube and the adaptor. Eventually, the adaptor, with its connection to the mechanical respirator, can dislodge from the plastic tube. The patient then loses, even if only temporarily, the assistance to his breathing or the anesthetic that he should receive.

Even while adhering, the tape itself causes additional problems. Many people have a mild to severe allergy to the tape's adhesive. Most hospitals, of course, do use, when necessary, a hypoallergenic tape. However, the need for such a tape for any particular individual does not become apparent until that patient has shown some reaction to the usual adhesive. By that time, the patient may have already developed significant dermatological problems.

Thus, although endotracheal tubes have provided definite advantages to patients undergoing surgery and when in need of respiratory assistance, the device needs constant attention. Additionally, a disoriented patient, while on a respirator, may himself dislodge the endotracheal tube. These problems become even more serious since the dislodgement and subsequent movement of the tube can traumatize a patient's vocal cords and trachea. Consequently, the effort continues to find an endotracheal device providing greater reliability and safety for the patient.

SUMMARY

Utilizing a narrow web of substantially nonadhesive material to retain an endotracheal tube in place alleviates the problems associated with adhesive tape. Furthermore, contact with mucus or saliva does not detract from its ability to retain the tube in its proper location. Without the adhesive, the web or ribbon of material, of course, will not induce an allergic reation with the patient's skin.

The ribbon should have sufficient length to extend around the head of the patient. To apply the ribbon, the attendant first attaches it to the endotracheal tube. Specifically, he couples it to a holding means attached to the adaptor. This holding means, when the ribbon extends around the patient's head, maintains the ribbon in proximity to the adaptor. The attendant then wraps and ties the ribbon around the head of the patient to keep it in place.

Typically, the holding device may take the form of flanges formed on the adaptor. Each flange should have an opening passing through it. Coupling the ribbon to the flanges involves passing the material through the openings in the flanges.

In addition to extending the ribbon around the patient's head, the attendant should also normally wrap it around the plastic tube portion of the endotracheal device. This helps retain the adaptor to the tube without the necessity of any adhesive which can lose its effectiveness upon attack by mucus and other fluids.

As an additional feature, the ribbon covers very little of the area of the patient's mouth surrounding the endotracheal tube. This permits, first, the attendant or nurse to care for the patient's mouth which accordingly remains uncovered. The security of the endotracheal tube's location also reduces the risk that such care would dislodge it. Furthermore, with the area around the mouth remaining uncovered, an attendant may more readily and safely perform tracheal and pharyngeal suctioning on the patient.

BRIEF DESCRIPTION OF THE FIGURES

FIG. 1 shows an endotracheal device in which the adaptor has flanges with holes passing through them for securing it to the patient.

FIG. 2 gives a side elevational view of the adaptor in FIG. 1.

FIG. 3 provides a top plan view of the adaptor with flanges having holes passing through them.

FIG. 4 shows the use and securement of the endotracheal device of FIG. 1 on patient.

FIG. 5 shows a method of wrapping the attaching ribbon around the endotracheal tube and through the openings in the flanges of the adaptor.

DETAILED DESCRIPTION

The endotracheal device, shown generally at 11 in FIG. 1, includes the plastic tube 12 with which the adaptor 13 has a press-fit coupling. The tapered end 14 of the tube 12 permits its facile insertion through the patient's mouth and into his trachea. The opening 15 with the end 14 provides a passageway to both of the patient's brachii should the tube 12 extend that far in the trachea.

Near the opening 14, the inflatable collar 17 surrounds the tube 12. Through a passageway formed in the tube 12, the collar 17 connects to the thin tubule 18. The tubule 18, in turn, extends to the bladder 19 which attaches to the plastic inlet 20. Once inserted into the patient's trachea, applying air to the inlet 20 inflates both the collar 17 and the bladder 19. The former expands against the patient's trachea to help secure the endotracheal device 11 in its proper position. The inflated bladder 19 indicates the state of inflation of the collar 17.

Once inflated, the cap 21, placed over the inlet 20, prevents the egress of the gas within the collar 17 and the bladder 19. Alternatively, the one-way valve 22 may find use in preventing the escape of gas from these components.

FIG. 2 shows the adaptor 13 including the narrow tube 25, which press fits into the plastic tube 12 of FIG. 1. The wider tube portion 26 of the adaptor 13 permits its coupling to mechanical respirating equipment.

The adaptor 13 also includes the flanges 29 and 30 to permit the secure attachment of the endotracheal device 11 to the patient. The flanges 29 and 30 have the openings 31 and 32, respectively, passing through them, as seen in FIG. 3. A ribbon of cloth passes through the openings 31 and 32 to secure the proper location of the adaptor 13 and, thus, the endotracheal device 11, in the patient.

The flanges 29 and 30, instead of completely surrounding the openings 31 and 32, respectively, could have small notches or passageways which would allow for the placement of the middle of the ribbon into the openings 31 and 32. This would eliminate the necessity of threading the ends of the ribbon through the openings 31 and 32 as with the adaptor 13 shown in FIG. 3. In either case, the adaptor 13 most conveniently results from the injection molding of a single integral piece including the flanges 29 and 30 and the small and large tubes 25 and 26.

To utilize the endotracheal device 11, the attendant inserts the tapered end 14 into the trachea 36 of the patient, as shown in FIG. 4. The adaptor 13, however remains at least partially extended beyond the patient's mouth. The attendant then places the ribbon of cloth 37 in proximity to the adaptor 13. He next threads it through the openings 31 and 32 of the flanges 29 and 30 to couple the ribbon 37 to the adaptor 13.

Either before or after threading the ribbon 37 through the openings 31 and 32, the attendant also wraps it around the tube 12 adjacent to the adaptor 13, as shown in FIG. 5. Conveniently, he can do this by placing a slip knot in the ribbon 37 and sliding the knot's opening over the flanges 29 and 30 until it reaches the end of the tube 12. He then tightens the slip knot in the ribbon 37 around the tube 12 and threads the ends of the ribbon 37 through the openings 31 and 32. Wrapping the ribbon 37 around the tube 12, in addition to placing it through the openings 31 and 32, assists in maintaining the proper connection between the adaptor 13 and the tube 12. This becomes important as the patient's saliva reaches the junction between these two components. This moisture could result in the two pieces, affixed to each other by only a press fit, separating. The ribbon 37, in contact with both components, helps prevent this deleterious result.

The attendant then wraps the ribbon 37 around and underneath the head of the patient. Tying the knot 38 completes the attachment of the endotracheal device 11 to the patient.

Accordingly, what is claimed is:

1. In an endotracheal device having a tube with first and second ends with said first end insertable through the mouth of a person and into that person's trachea, the improvement comprising:
    (A) an adaptor, coupled to and removable from said second end of said tube, said adaptor being adapted to couple to mechanical respirating equipment;
    (B) a narrow elongated web of substantially nonadhesive material of sufficient length to extend around said tube and around the head of said person; and
    (C) holding means, attached to said adaptor, for maintaining said web, when around said tube and around the head of said person, in proximity to said adaptor.

2. The improvement of claim 1 wherein said holding means includes two flanges coupled to said adaptor with each of said flanges having an opening therethrough sufficiently large to allow the passage through said opening of said web of material.

3. The improvement of claim 2 wherein said flanges are formed integrally with said adaptor.

4. The improvement of claim 3 wherein said web of material is a thin ribbon of cloth.

5. A method for placing within the trachea of a person an endotracheal device having:
    (a) a tube with first and second ends with said first end insertable through the mouth of a person and into that person's trachea; and
    (b) an adaptor, coupled to and removable from said second end of said tube, said adaptor being adapted to couple to mechanical respirating equipment;
    (c) holding means, attached to said adaptor, for coupling to and maintaining a narrow, elongated web of material in proximity to said adaptor,
said method comprising:
    (A) inserting said first end of said tube through said person's mouth and into that person's trachea with at least part of said adaptor remaining extended from said person's mouth;
    (B) placing a narrow, elongated, substantially nonadhesive web of material in proximity to said adaptor;
    (C) coupling said nonadhesive web to said holding means;
    (D) wrapping said nonadhesive web around said second end of said tube;
    (E) wrapping said nonadhesive web around the head of said person; and
    (F) tying the ends of said web together.

6. The method of claim 5 wherein said holding means includes at least one flange formed integrally with said adaptor and having a hole therethrough, said hole through said flange being sufficiently large to allow the passage therethrough of said web and wherein said step of coupling said web to said holding means is accomplished by placing said web through said opening.

* * * * *